United States Patent
Kanai et al.

(10) Patent No.: US 7,393,135 B2
(45) Date of Patent: Jul. 1, 2008

(54) MOISTURE DETECTION DEVICE

(75) Inventors: Yoshiyuki Kanai, Tokyo (JP); Kazumasa Ibata, Tokyo (JP); Shigeki Shoji, Tokyo (JP); Masaki Takechi, Tokyo (JP); Shingo Masumoto, Tokyo (JP); Toshio Kurihara, Tokyo (JP)

(73) Assignee: Yamatake Corporation, Tokyo (JP)

( * ) Notice: Subject to any disclaimer, the term of this patent is extended or adjusted under 35 U.S.C. 154(b) by 0 days.

(21) Appl. No.: 10/593,907

(22) PCT Filed: Mar. 16, 2005

(86) PCT No.: PCT/JP2005/004648

§ 371 (c)(1),
(2), (4) Date: Sep. 20, 2006

(87) PCT Pub. No.: WO2005/098403

PCT Pub. Date: Oct. 20, 2005

(65) Prior Publication Data

US 2007/0211781 A1    Sep. 13, 2007

(30) Foreign Application Priority Data

Mar. 30, 2004    (JP) .............................. 2004-101415

(51) Int. Cl.
*G01N 25/02*    (2006.01)
(52) U.S. Cl. .................. 374/19; 73/29.01; 73/29.02
(58) Field of Classification Search .................. 374/19; 73/29.01, 29.02
See application file for complete search history.

(56) References Cited

U.S. PATENT DOCUMENTS

| 3,528,278 | A | | 9/1970 | Sterling |
| 4,083,224 | A | * | 4/1978 | Gayst ............................ 374/19 |
| 4,946,288 | A | * | 8/1990 | Siska et al. .................... 374/20 |
| 6,250,134 | B1 | * | 6/2001 | Ruppert ...................... 73/29.01 |
| 6,926,439 | B2 | * | 8/2005 | Zlochin ........................ 374/20 |

FOREIGN PATENT DOCUMENTS

| JP | 61-075235 A | 4/1986 |
| JP | 07-104304 B | 11/1996 |
| JP | 3194108 B | 6/2001 |
| JP | 2004-108940 A | 4/2004 |

* cited by examiner

*Primary Examiner*—Gail Verbitsky
*Assistant Examiner*—Megann E Vaughn
(74) *Attorney, Agent, or Firm*—Blakely, Sokoloff, Tayor & Zafman LLP

(57) ABSTRACT

Very small projections (10-2) are arranged on a mirror surface (10-1) of a mirror (10). The shape of a projection (10-2) is not limited to a circular cone, but it can be a hollow-cylindrical shape, semispherical shape, or square prism shape, and also, it can be a polyhedron with many faces. With a reduction in temperature of the mirror (10), water vapor contained in a gas to be measured condenses on the mirror surface (10-1) of the mirror (10). In this case, because of the very small projections (10-2) on the mirror surface (10-1), the condensation is promoted by the projections (10-2) serving as the cores. This facilitates condensation even at low dew points and improves response. Further, the size of condensation products does not easily vary relative to variation in flow speed of the gas to be measured, and this makes equilibrium of condensation less likely to break, increasing measurement accuracy.

6 Claims, 8 Drawing Sheets

MOISTURE DETECTION DEVICE

The present patent application is a non-provisional application claiming the benefit of International Application No. PCT/JP2005/004648, filed Mar. 16, 2005.

BACKGROUND OF THE INVENTION

The present invention relates to a moisture detection device which detects moisture which is produced on a mirror surface and contained in a gas to be measured.

BACKGROUND ART

As a conventional humidity measurement method, a dew point detection method of detecting a dew point by lowering the temperature of a gas to be measured and measuring a temperature at which part of water vapor contained in the gas condenses is known. For example, reference 1 (industrial measurement handbook, Asakura Publishing Co., Ltd., Sep. 30, 1976, p. 297) discloses a chilled mirror dew point hygrometer which detects the dew point of moisture in a gas to be measured by chilling a mirror by using a refrigerant, freezer, electronic refrigerator, or the like, detecting a change in the intensity of reflected light on the chilled mirror surface, and measuring the temperature of the mirror surface at this point of time.

Such chilled mirror dew point hygrometers are categorized into two types according to the type of reflected light to be used. One type is based on a specular reflection detection scheme using specular reflection as disclosed in reference 2 (Japanese Patent Laid-Open No. 61-75235). The other type is based on a scattered light detection scheme using scattered light as disclosed in reference 3 (Japanese Patent Publication NO. 7-104304).

Specular Reflection Detection Scheme

FIG. 10 shows the main part of a conventional chilled mirror dew point hygrometer using the specular reflection detection scheme. A chilled mirror dew point hygrometer 101 comprises a chamber 1 in which a gas to be measured is caused to flow and a thermoelectric cooling element (Peltier element) 2 provided in the chamber 1. A bolt 4 is mounted on a cooling surface 2-1 of the thermoelectric cooling element 2 through a copper block 3, and a radiator fin 5 is mounted on a heating surface 2-2 of the thermoelectric cooling element 2. An upper surface 4-1 of the bolt 4 mounted on the copper block 3 is a mirror surface. A wire-wound resistance temperature detector (temperature detection element) 6 is embedded in a side portion of the copper block 3 (see FIG. 12). A light-emitting element 7 which obliquely applies light to the upper surface (mirror surface) 4-1 of the bolt 4 and a light-receiving element 8 which receives specular reflection of light applied from the light-emitting element 7 to the upper surface 4-1 are mounted in the upper portion of the chamber 1. A heat insulation material 40 is provided around the thermoelectric cooling element 2.

In the chilled mirror dew point hygrometer 101, the mirror surface 4-1 in the chamber 1 is exposed to the gas to be measured which is caused to flow into the chamber 1. If no dew condensation has occurred on the mirror surface 4-1, almost the entire amount of light emitted from the light-emitting element 7 is specularly reflected, and received by the light-receiving element 8. If, therefore, no dew condensation has occurred on the mirror surface 4-1, the reflected light received by the light-receiving element 8 has a high intensity.

As the temperature of the cooling surface 2-1 of the thermoelectric cooling element 2 is lowered by increasing the current to the thermoelectric cooling element 2, water vapor contained in a gas to be measured condenses into water on the mirror surface 4-1, and part of light emitted from the light-emitting element 7 is absorbed and reflected diffusely by the molecules of the water. As a consequence, the intensity of the reflected light (specular reflection) received by the light-receiving element 8 decreases. Detecting a change in specular reflection on the mirror surface 4-1 makes it possible to know a change in state on the mirror surface 4-1, i.e., the adhesion of moisture (water droplets) onto the mirror surface 4-1. In addition, the dew point of moisture in the gas to be measured can be known by indirectly measuring the temperature of the 4-chamber 1 using the temperature detection element 6.

Scattered Light Detection Scheme

FIG. 11 shows the main part of a conventional chilled mirror dew point hygrometer using the scattered light detection scheme. A chilled mirror dew point hygrometer 102 has almost the same arrangement as that of the chilled mirror dew point hygrometer 101 using the specular reflection detection scheme except for the mount position of the light-receiving element 8. In the chilled mirror dew point hygrometer 102, the light-receiving element 8 is placed at a position to receive scattered light instead of a position to receive specular reflection of light applied from the light-emitting element 7 to the mirror surface 4-1.

In the chilled mirror dew point hygrometer 102, the mirror surface 4-1 is exposed to a gas to be measured which is caused to flow into the chamber 1. If no dew condensation has occurred on the mirror surface 4-1, almost the entire amount of light emitted from the light-emitting element 7 is specularly reflected, and the amount of light received by the light-receiving element 8 is very small. If no dew condensation has occurred on the mirror surface 4-1, the reflected light received by the light-receiving element 8 has a low intensity.

As the temperature of the cooling surface 2-1 of the thermoelectric cooling element 2 is lowered by increasing the current to the thermoelectric cooling element 2, water vapor contained in the gas to be measured condenses into water on the mirror surface 4-1. Part of light emitted from the light-emitting element 7 is absorbed and reflected diffusely by the molecules of the water. As a consequence, the intensity of light (scattered light) reflected diffusely by the light-receiving element 8 increases. Detecting a change in scattered light on the mirror surface 4-1 makes it possible to know a change in state on the mirror surface 4-1, i.e., the adhesion of moisture (water droplets) on the mirror surface 4-1. In addition, the dew point of moisture in the gas to be measured can be known by indirectly measuring the temperature of the mirror surface 4-1 using the temperature detection element 6.

The above hygrometer is described by taking, as an example, the detection of dew condensation (moisture) which occurs on the mirror surface 4-1. However, the same arrangement can detect frost formation (moisture) which occurs on the mirror surface 4-1.

SUMMARY OF THE INVENTION

However, in either of the above conventional chilled mirror dew point hygrometers 101 and 102, the surface of the mirror (mirror surface) is as smooth as possible to achieve better reflection. More specifically, for example, such hygrometers have used a mirror made of copper plated with rhodium and a mirror made of platinum. Some other hygrometers have used, as a mirror, a silicon wafer having an upper surface on which aluminum is deposited and then a thin aluminum nitride film is coated thereon.

As described above, in such a conventional chilled mirror dew point hygrometer, since the mirror surface of the mirror is smooth, there is no source for dew condensation or frost formation. For this reason, in dew point measurement for a very low dew point, it takes much time until dew condensation or frost formation occurs, resulting in poor responsiveness. In addition, a change in the flow rate of a gas to be measured which flows on the mirror surface disturbs the equilibrium state of dew condensation, resulting in poor measurement accuracy.

The present invention has been made to solve such problems, and has as its object to provide a mirror surface state detection device and moisture detection device which have good responsiveness and can improve measurement accuracy.

MEANS OF SOLUTION TO THE PROBLEM

In order to achieve the above object, according to the present invention, there is provided a moisture detection device comprising a mirror whose mirror surface is exposed to a gas to be measured, minute projections formed on the mirror surface of the mirror, cooling means for cooling the mirror, light-emitting means for applying light to the mirror surface, light-receiving means for receiving reflected light of light applied from the light-emitting means to the mirror surface, and means for detecting moisture which is produced on the mirror surface of the mirror which is cooled by the cooling means on the basis of the reflected light received by the light-receiving means.

According to the present invention, the light-emitting means applies light to the mirror surface of the mirror, and the light-receiving means receives reflected light (specular reflection in the case of the specular reflection detection scheme or scattered light in the case of the scattered light detection scheme) of the applied light from the mirror surface. Moisture (e.g., condensed dew or formed frost) produced on the mirror surface of the mirror cooled by the cooling means is detected on the basis of the reflected light received by the light-receiving means. In this case, since the minute projections are formed on the mirror surface of the mirror, the projections serve as nuclei to promote dew condensation or frost formation.

EFFECTS OF THE INVENTION

According to the present invention, since the minute projections are formed on the mirror surface of the mirror, the projections serve as nuclei to promote dew condensation or frost formation, thereby improving responsiveness and measurement accuracy.

DETAILED DESCRIPTION OF THE INVENTION

The present invention will be described in detail with reference to the accompanying drawings.

First Embodiment

Chilled Mirror Dew Point Hygrometer (Scattered Light Detection Scheme)

Figure 1:
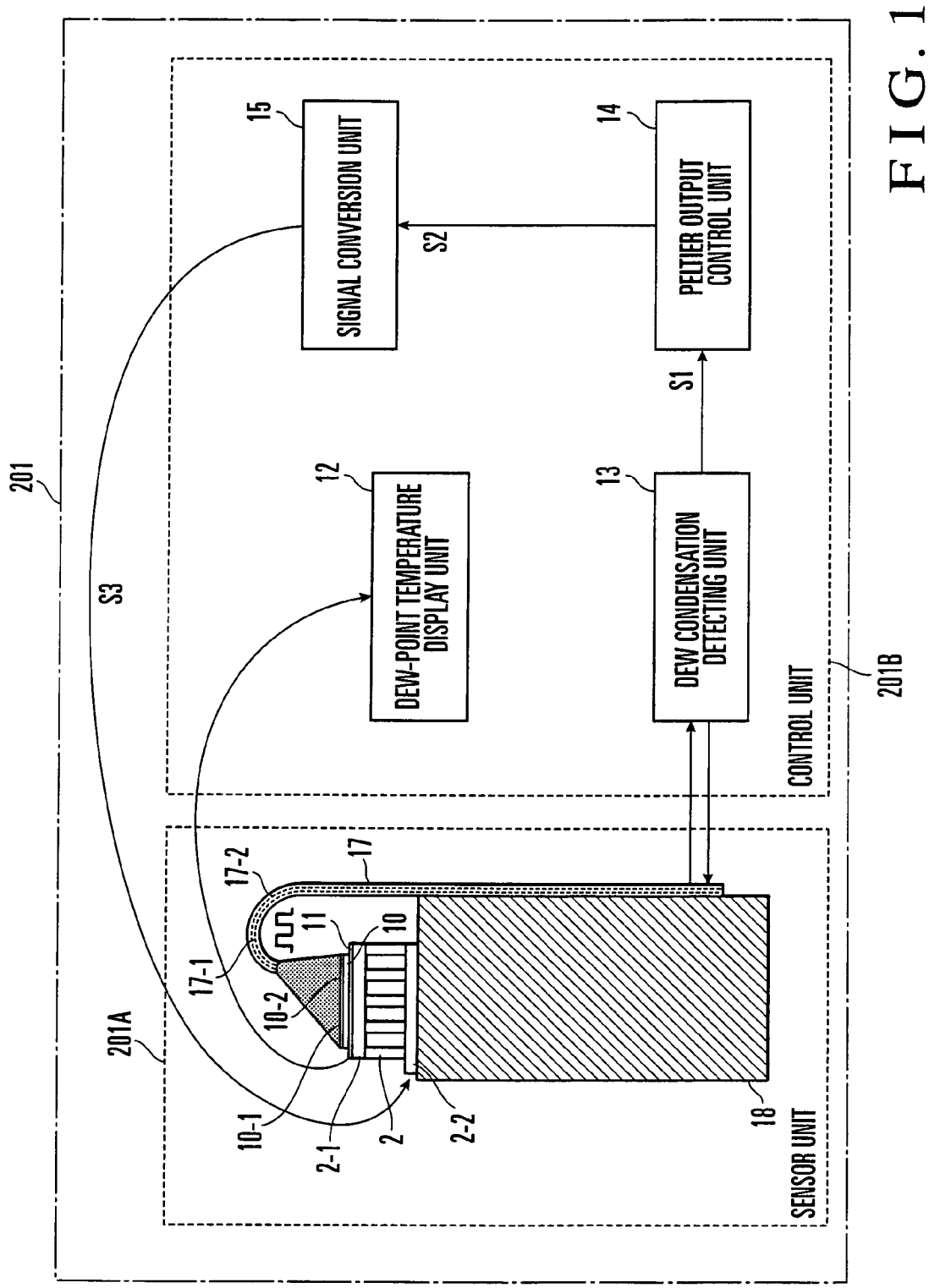
FIG. 1 is a schematic view of the arrangement of a chilled mirror dew point hygrometer showing an embodiment (first embodiment) of a moisture detection device according to the present invention.

FIG. 1 is a schematic view showing the arrangement of a chilled mirror dew point hygrometer showing an embodiment of a moisture detection device according to the present invention. A chilled mirror dew point hygrometer 201 includes a sensor unit 201A and a control unit 201B.

In the sensor unit 201A, a mirror 10 is mounted on a cooling surface 2-1 of a thermoelectric cooling element (Peltier element) 2. The mirror 10 comprises, for example, a silicon chip, which has a surface 10-1 as a mirror surface. A thin-film resistance temperature detector (temperature detection element) 11 made of, for example, platinum is formed on the joint surface between the mirror 10 and the cooling surface 2-1 of the thermoelectric cooling element 2. A columnar heat sink 18 is joined to a heating surface 2-2 of the thermoelectric cooling element 2, and a tube 17 made of stainless steel having its upper end portion bent in the form of the letter "J" along the heat sink 18 is provided.

Figure 2A:
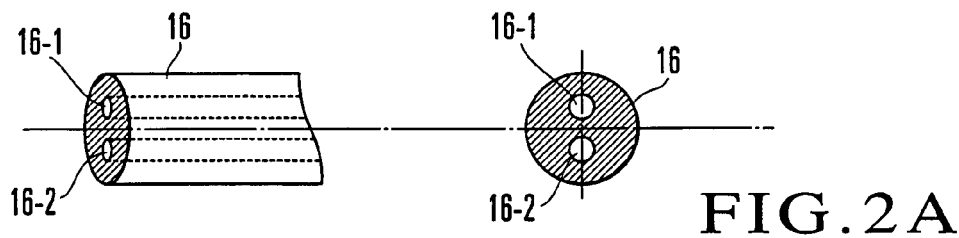
FIG. 2A is a view exemplifying the arrangement in which an optical fiber on the light-emitting side and an optical fiber on the light-receiving side are coaxially provided in one tube.
Figure 2B:
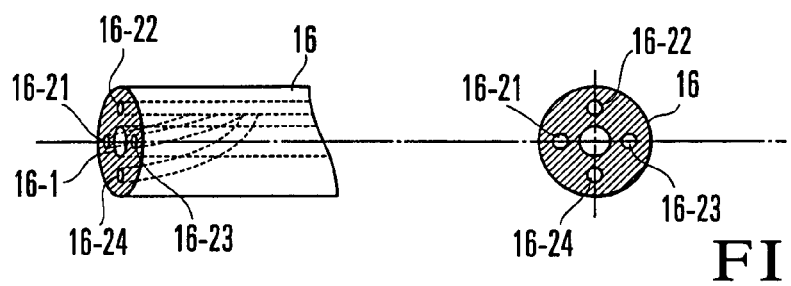
FIG. 2B is a view exemplifying the arrangement in which an optical fiber on the light-emitting side and optical fibers on the light-receiving side are coaxially provided in one tube.
Figure 2C:
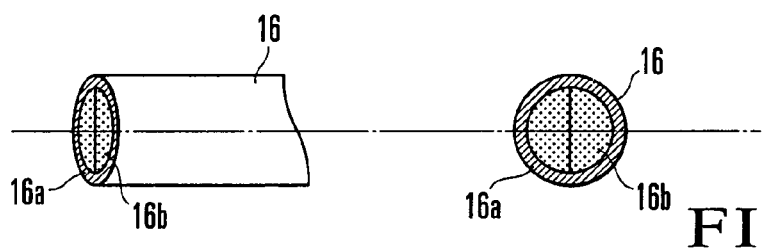
FIG. 2C is a view exemplifying the arrangement in which an optical fiber on the light-emitting side and an optical fiber on the light-receiving side are coaxially provided in one tube.
Figure 2D:
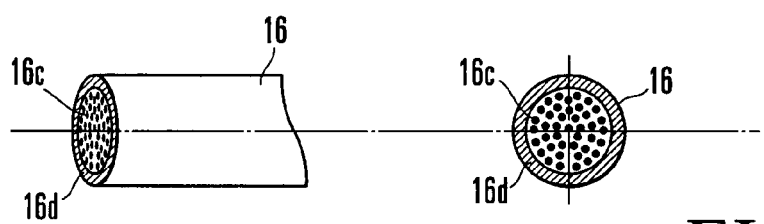
FIG. 2D is a view exemplifying the arrangement in which optical fibers on the light-emitting side and optical fibers on the light-receiving side are coaxially provided in one tube.
Figure 2E:
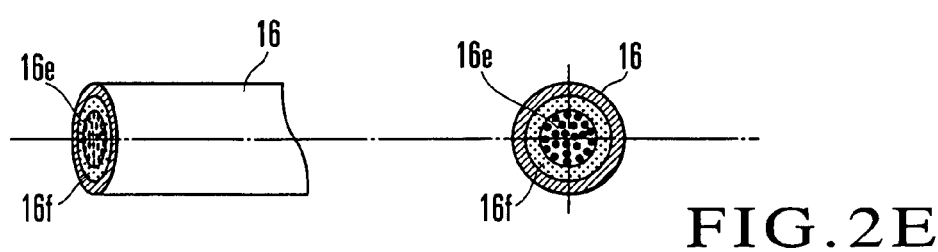
FIG. 2E is a view exemplifying the arrangement in which an optical fiber on the light-emitting side and optical fibers on the light-receiving side are coaxially provided in one tube.

As the tube 17, one of tubes 16 accommodating optical fibers in various forms like those shown in FIGS. 2A to 2E can be used. Referring to FIG. 2A, the tube 16 coaxially accommodates an optical fiber 16-1 on the light-emitting side and an optical fiber 16-2 on the light-receiving side. Referring to FIG. 2B, the tube 16 coaxially accommodates an optical fiber 16-1 on the light-emitting side (or the light-receiving side) and optical fibers 16-21 to 16-24 on the light-receiving side (or the light-emitting side). Referring to FIG. 2C, in the tube 16, the left half portion is formed into an optical fiber 16a on the light-emitting side, and the right half portion is formed into an optical fiber 16b on the light-receiving side. Referring to FIG. 2D, the tube 16 accommodates optical fibers 16c on the light-emitting side and optical fibers 16d on the light-receiving side in a mixed state. Referring to FIG. 2E, in the tube 16, the central portion accommodates optical fibers 16e on the light-emitting side (or the light-receiving side), and an optical fiber 16f on the light-receiving side (or the light-emitting side) is placed around the optical fibers 16e.

The chilled mirror dew point hygrometer 201 shown in FIG. 1 uses the tube 16 shown in FIG. 2A as the tube 17, which accommodates an optical fiber 17-1 on the light-emitting side and an optical fiber 17-2 on the light-receiving side. The distal end portions (the light-emitting and light-receiving portions) of the optical fiber 17-1 on the light-emitting side and optical fiber 17-2 on the light-receiving side, which are bend in the form of the letter "J", are directed to the mirror surface 10-1 of the mirror 10, and are tilted at a predetermined angle with respect to the mirror surface 10-1. As a consequence, the applying direction (optical axis) of light from the optical fiber 17-1 and the receiving direction (optical axis) of light in the optical fiber 17-2 are made parallel to each other, and are placed adjacent to each other at the same tilt angle.

Figure 3:
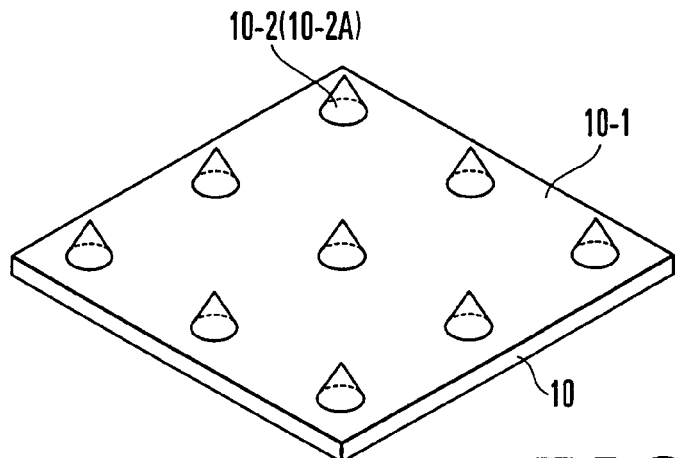
FIG. 3 is a view showing minute projections formed on the mirror surface of a mirror.
Figure 4A:
FIG. 4A is a view showing a modification of the minute projection.
Figure 4B:
FIG. 4B is a view showing a modification of the minute projection.
Figure 4C:
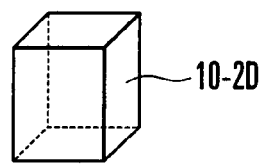
FIG. 4C is a view showing a modification of the minute projection.
Figure 4D:
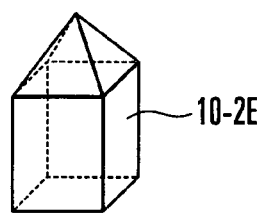
FIG. 4D is a view showing a modification of the minute projection.

In this embodiment, as shown in FIG. 3, the mirror surface 10-1 of the mirror 10 is provided with a plurality of minute conical projections (projecting portions) 10-2 (10-2A). The projections 10-2 are formed by, for example, using a photoresist and etching, and vary in size (height and diameter) and interval depending on the diameters of dew drops to be generated. For example, the diameter of each projection is set to about 0.1 to 1 µm; the height, to about 0.1 to 1 µm; and the interval, to about 10 to 50 µm. The shape of the projection 10-2 is not limited to a conical shape. For example, a cylindrical projection 10-2B like the one shown in FIG. 4A, a semispherical projection 10-2C like the one shown in FIG. 4B, a projection 10-2D in the form of a quadratic prism like the one shown in FIG. 4C, or a polyhedral projection 10-2E having many surfaces may be used.

The control unit 201B comprises a dew-point temperature display unit 12, dew condensation detecting unit 13, Peltier output control unit 14, and signal conversion unit 15. The dew-point temperature display unit 12 displays the temperature of the mirror 10 which is detected by the temperature detection element 11. The dew condensation detecting unit 13 obliquely applies pulse light from the distal end portion of the optical fiber 17-1 to the mirror surface 10-1 of the mirror 10 at a predetermined period, obtains the difference between the upper and lower limit values of reflected pulse light (scattered light) received through the optical fiber 17-2 as the intensity of the reflected pulse light, and sends a signal S1 corresponding to the intensity of the reflected pulse signal to the Peltier output control unit 14. The Peltier output control unit 14 receives the signal S1 from the dew condensation detecting unit 13, and compares the intensity of the reflected pulse light with a predetermined threshold. If the intensity of the reflected pulse light has not reached the threshold, the Peltier output control unit 14 outputs, to the signal conversion unit 15, a control signal S2 for increasing the current to the thermoelectric cooling element 2 in accordance with the value of the signal S1. If the intensity of the reflected pulse light exceeds the threshold, the Peltier output control unit 14 outputs, to the signal conversion unit 15, the control signal S2 for decreasing the current to the thermoelectric cooling element 2 in accordance with the value of the signal S1. The signal conversion unit 15 supplies a current S3 designated by the control signal S2 from the Peltier output control unit 14 to the thermoelectric cooling element 2.

Figure 5A:
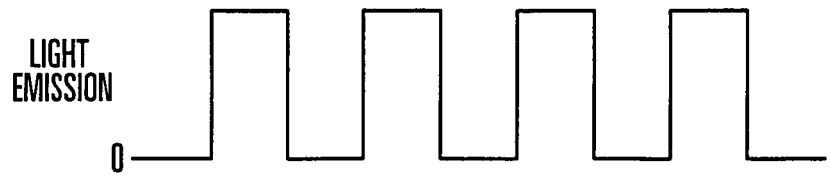
FIG. 5A is a waveform chart of pulse light applied to the mirror surface.

In the chilled mirror dew point hygrometer 201, the sensor unit 201A is placed in a gas to be measured. The dew condensation detecting unit 13 obliquely applies pulse light from the distal end portion of the optical fiber 17-1 to the mirror surface 10-1 of the mirror 10 at a predetermined period (see FIG. 5A). The mirror surface 10-1 is exposed to the gas to be measured. If no dew condensation has occurred on the mirror surface 10-1, almost the entire amount of pulse light applied from the distal end portion of the optical fiber 17-1 is specularly reflected, and hence the amount of reflected pulse light (scattered light) received from the mirror surface 10-1 through the optical fiber 17-2 is very small. Therefore, if no dew condensation has occurred on the mirror surface 10-1, the reflected pulse light received through the optical fiber 17-2 has a low intensity.

The dew condensation detecting unit 13 obtains the difference between the upper and lower limit values of reflected pulse light received through the optical fiber 17-2 as the intensity of the reflected pulse light, and sends the signal S1 corresponding to the intensity of the reflected pulse light to the Peltier output control unit 14. In this case, the intensity of the reflected pulse light is almost zero and has not reached the threshold, and hence the Peltier output control unit 14 sends, to the signal conversion unit 15, the control signal S2 for increasing the current to the thermoelectric cooling element 2. With this operation, the current S3 from the signal conversion unit 15 to the thermoelectric cooling element 2 increases to lower the temperature of the cooling surface 2-1 of the thermoelectric cooling element 2.

As the temperature of the cooling surface 2-1 of the thermoelectric cooling element 2, i.e., the temperature of the mirror 10, lowers, water vapor contained in the gas to be measured condenses on the mirror surface 10-1 of the mirror 10. At this time, in the dew point hygrometer according to this embodiment, the minute projections 10-2 provided on the mirror surface 10-1 of the mirror 10 serve as nuclei to promote dew condensation. The following is a reason why the projections 10-2 serve as nuclei to promote dew condensation. This reason will be described by exemplifying a case wherein water vapor in the air is formed into cloud. When water vapor in the air is formed into cloud, the vapor condenses around aerosols (which have a diameter of 0.2 µm or less and are also called dust or condensation nuclei) to form cloud. No cloud is formed in the air containing no aerosol. Likewise, the minute projections 10-2 provided on the mirror surface 10-1 serve as aerosols to make it easy for the water vapor contained in the gas to be measured to condense on the mirror surface 10-1.

Figure 6:
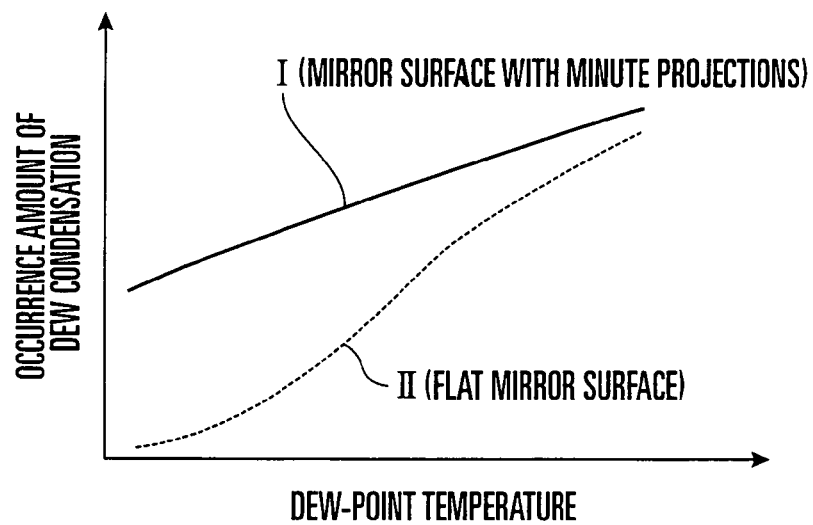
FIG. 6 is a graph showing the relationships between dew-point temperatures and the occurrence amounts of dew condensation in the case of a mirror surface with minute projections and in the case of a flat mirror surface.

FIG. 6 shows the relationships between dew-point temperatures and the occurrence amounts of dew condensation in the case of the mirror with the minute projections, which is obtained by providing the projections 10-2 on the mirror surface 10-1, and in the case of a flat mirror without the projections 10-2. A characteristic curve I in FIG. 6 is obtained in the case of the mirror surface with the minute projections, and a characteristic curve II is obtained in the case of the flat mirror. As is obvious from the comparison between the characteristic curves I and II, forming a mirror with minute projections makes it easy to cause dew condensation even at a low dew point as compared with the flat mirror. This improve responsiveness at a low dew point.

Figure 7:
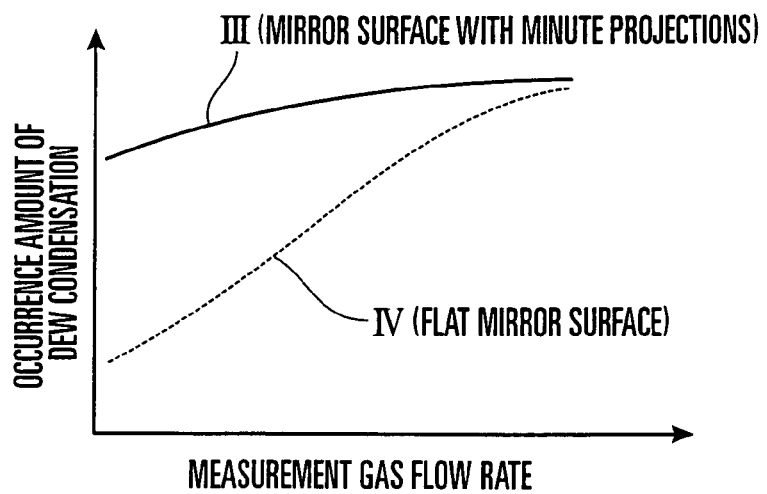
FIG. 7 is a graph showing the relationships between the flow rates of a gas to be measured (measurement gas flow rates) and the occurrence amounts of dew condensation in the case of the mirror surface with the minute projections and in the case of the flat mirror surface.

FIG. 7 shows the relationships between the flow rates of a gas to be measured (measurement gas flow rates) and the occurrence amounts of dew condensation in the case of the mirror with the minute projections, which is obtained by providing the projections 10-2 on the mirror surface 10-1, and in the case of the flat mirror without the projections 10-2. A characteristic curve III in FIG. 7 is obtained in the case of the mirror surface with the minute projections, and a characteristic curve IV is obtained in the case of the flat mirror. As is obvious from the comparison between the characteristic curves III and IV, forming a mirror with minute projections makes it possible to more stabilize the occurrence amount of dew condensation with a change in the flow rate of a gas to be measured than forming a flat mirror surface. This makes the sizes of condensed dew drops unlikely to change with a change in the flow rate of the gas to be measured, and makes the equilibrium state of dew condensation unlikely to break, thereby improving measurement accuracy.

When water vapor contained in the gas to be measured condenses into water on the mirror surface 10-1 of the mirror 10, part of pulse light applied from the distal end portion of the optical fiber 17-1 is absorbed and scatter by the molecules of the water. As a consequence, the intensity of the reflected pulse light (scattered light) from the mirror surface 10-1 which is received through the optical fiber 17-2 increases.

Figure 5B:
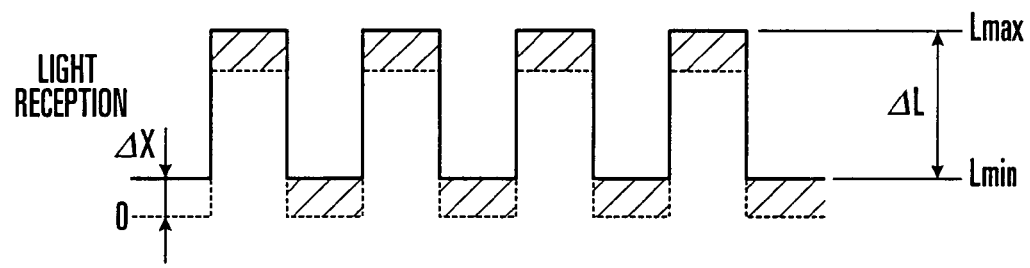
FIG. 5B is a waveform chart of reflected pulse light received from the mirror surface.

The dew condensation detecting unit 13 obtains the difference between the upper and lower limit values of each pulse of received reflected pulse light, and sets it as the intensity of reflected pulse light. That is, as shown in FIG. 5B, the dew condensation detecting unit 13 obtains a difference ΔL between an upper limit value Lmax and a lower limit value Lmin of one pulse of reflected pulse light, and sets it as the intensity of reflected pulse light. With this processing by the dew condensation detecting unit 13, disturbance light ΔX contained in the reflected pulse light is removed to prevent an operation error due to the disturbance light. The processing scheme of preventing an operation error due to disturbance light by using the pulse light detected by the dew condensation detecting unit 13 will be called a pulse modulation scheme. This processing makes it possible to omit a chamber from the sensor unit 201A in the chilled mirror dew point hygrometer 201.

Strictly speaking, even if no dew condensation has occurred, diffuse reflection is caused by the projections 10-2 provided on the mirror surface 10-1, and the resultant scattered light is received through the optical fiber 17-2. Since this light reception amount is constant, only an increase in scattered light due to dew condensation can be obtained by subtracting the light reception amount from the difference ΔL between the upper limit value Lmax and the lower limit value Lmin of one pulse.

If the intensity of reflected pulse light received through the optical fiber 17-2 exceeds the threshold, the Peltier output control unit 14 sends, to the signal conversion unit 15, the control signal S2 for decreasing the current to the thermoelectric cooling element 2. This suppresses a drop in the temperature of the cooling surface 2-1 of the thermoelectric cooling element 2 and the occurrence of dew condensation. With this suppression of dew condensation, the intensity of reflected pulse light received through the optical fiber 17-2 decreases. If the intensity becomes lower than the threshold, the Peltier output control unit 14 sends, to the signal conversion unit 15, the control signal S2 for increasing the current to the thermoelectric cooling element 2. Repeating this operation adjusts the temperature of the cooling surface 2-1 of the thermoelectric cooling element 2 so as to make the intensity of the reflected pulse light received through the optical fiber 17-2 become almost equal to the threshold. The adjusted temperature, i.e., the temperature (dew-point temperature) at which the dew condensation which has occurred on the mirror surface 10-1 has reached an equilibrium state is displayed as a dew-point temperature on the dew-point temperature display unit 12.

Figure 8:
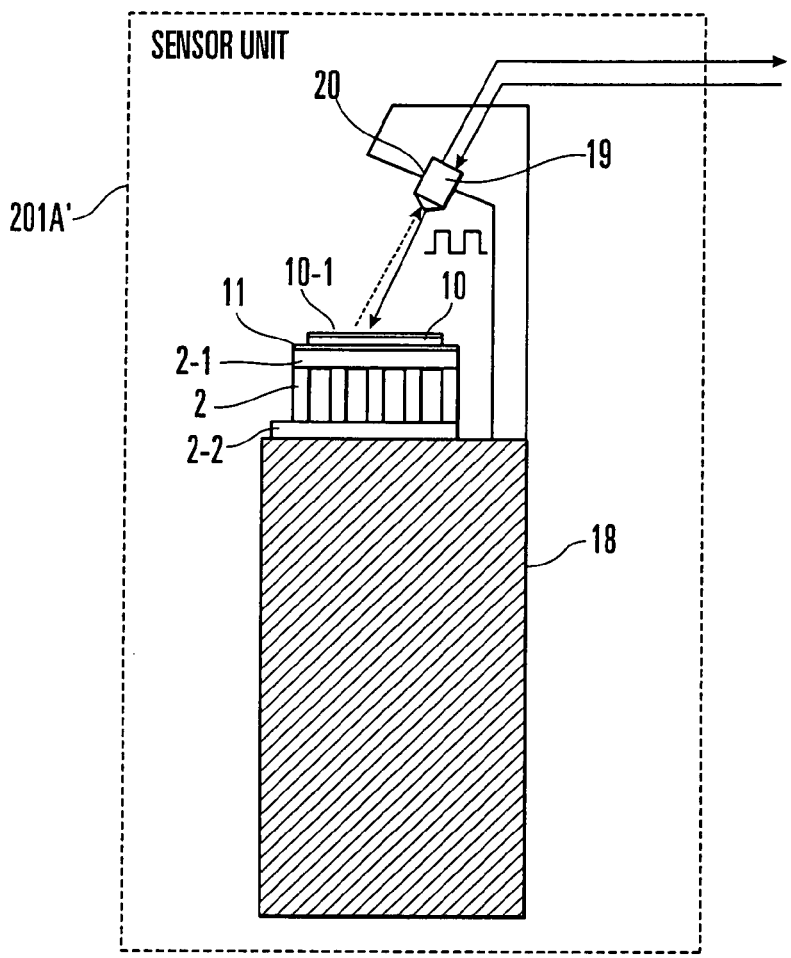
FIG. 8 is a view showing a modification of the chilled mirror dew point hygrometer according to the first embodiment.

In the chilled mirror dew point hygrometer 201 shown in FIG. 1, the sensor unit 201A uses the optical fiber 17-1 on the light-emitting side and the optical fiber 17-2 on the light-receiving side. However, like a sensor unit 201A' shown in FIG. 8, the sensor unit may use a light-emitting diode 19 instead of the optical fiber 17-1 on the light-emitting side, and a photocoupler 20 instead of the optical fiber 170-2 on the light-receiving side.

Second Embodiment

Chilled Mirror Dew Point Hygrometer 201 (Specular Reflection Detection Scheme)

Figure 9:
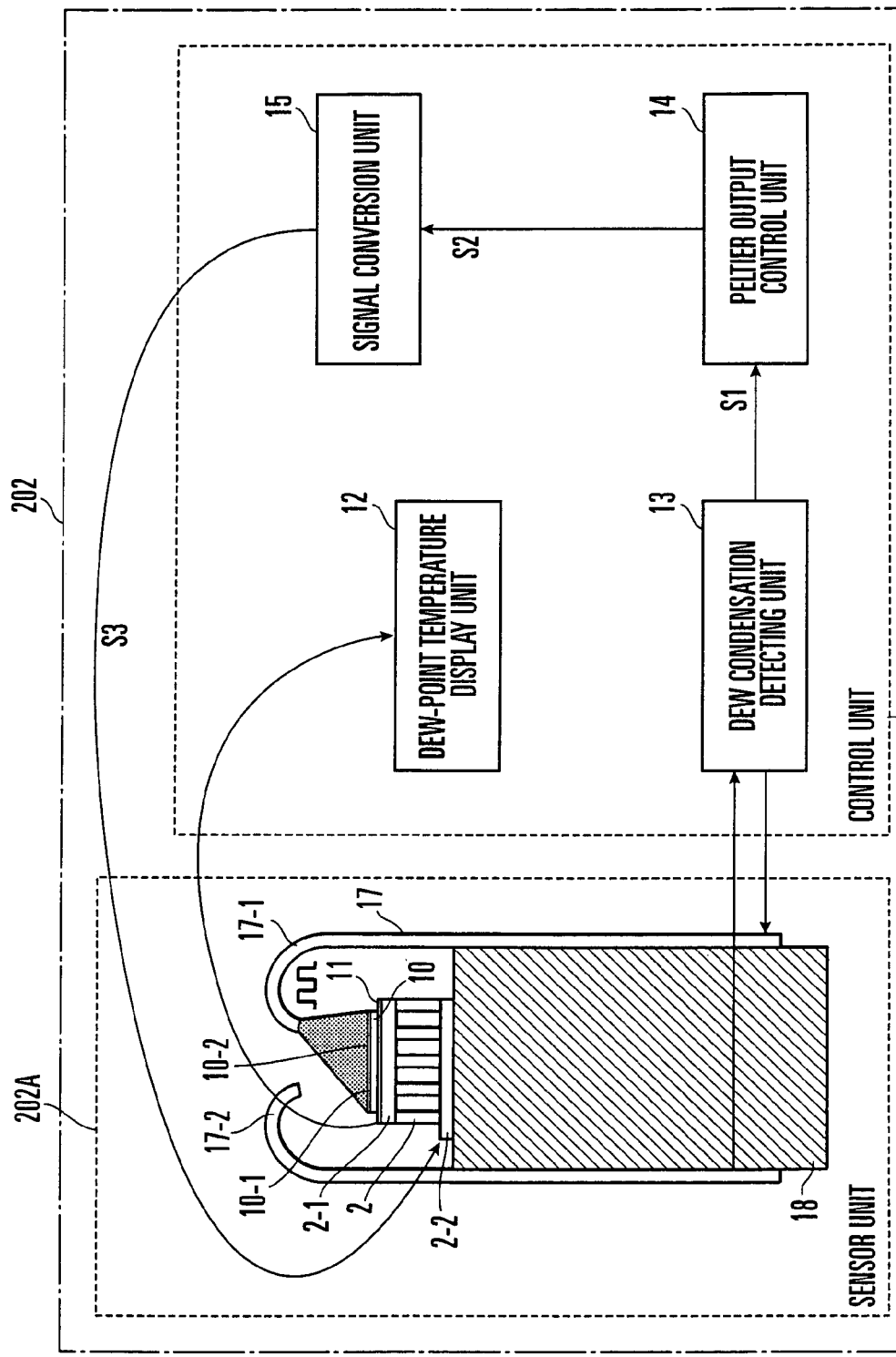
FIG. 9 is a schematic view showing the arrangement of a chilled mirror dew point hygrometer showing another embodiment (second embodiment) of the moisture detection device according to the present invention.
Figure 10:
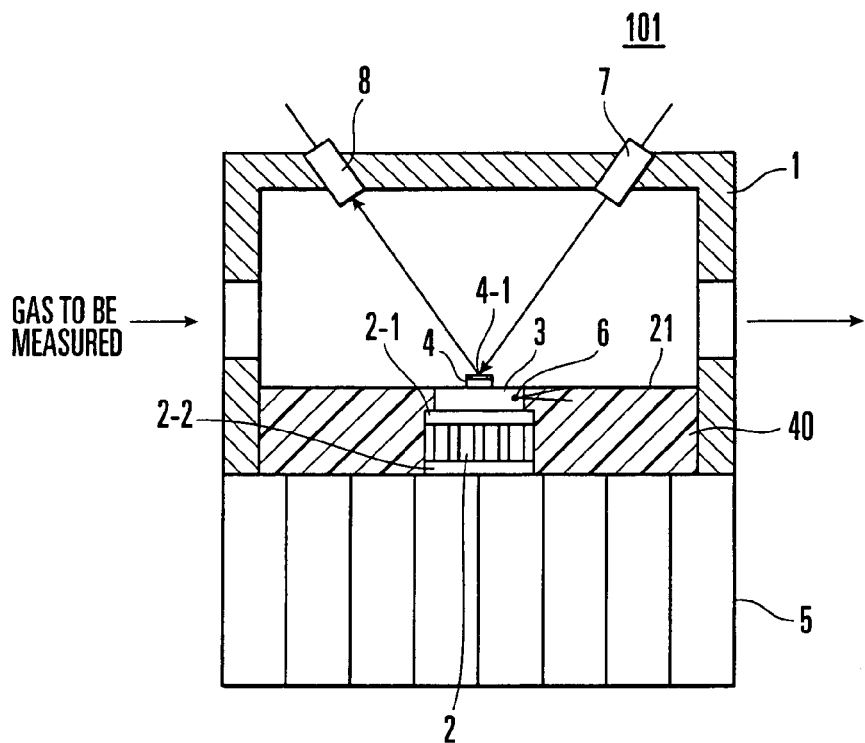
FIG. 10 is a view showing the main part of a conventional chilled mirror dew point hygrometer using the specular reflection detection scheme.
Figure 11:
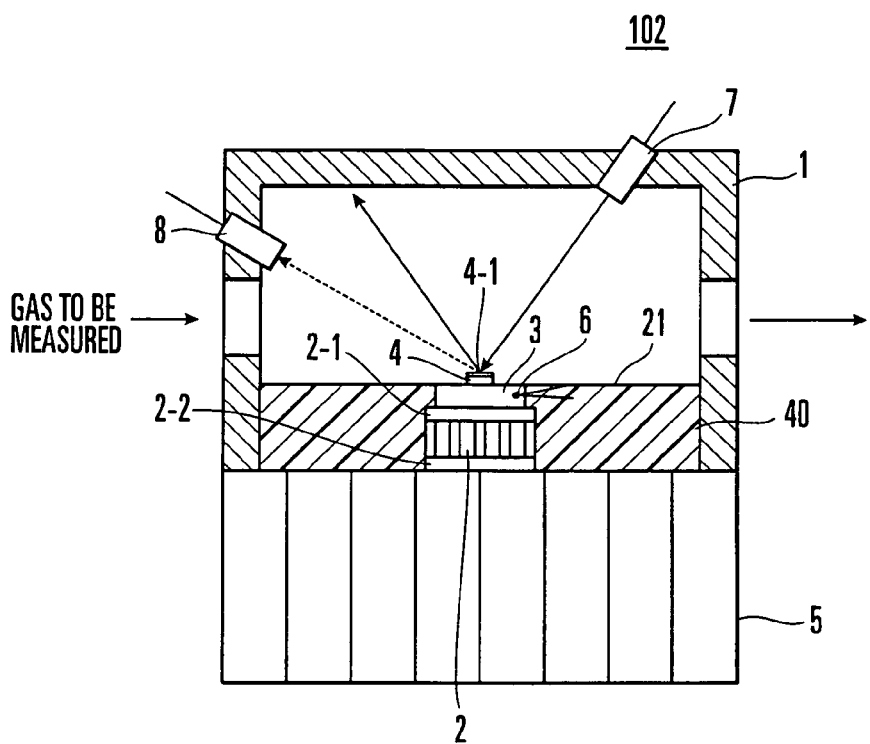
FIG. 11 is a view showing the main part of a conventional chilled mirror dew point hygrometer using the scattered light detection scheme.
Figure 12:
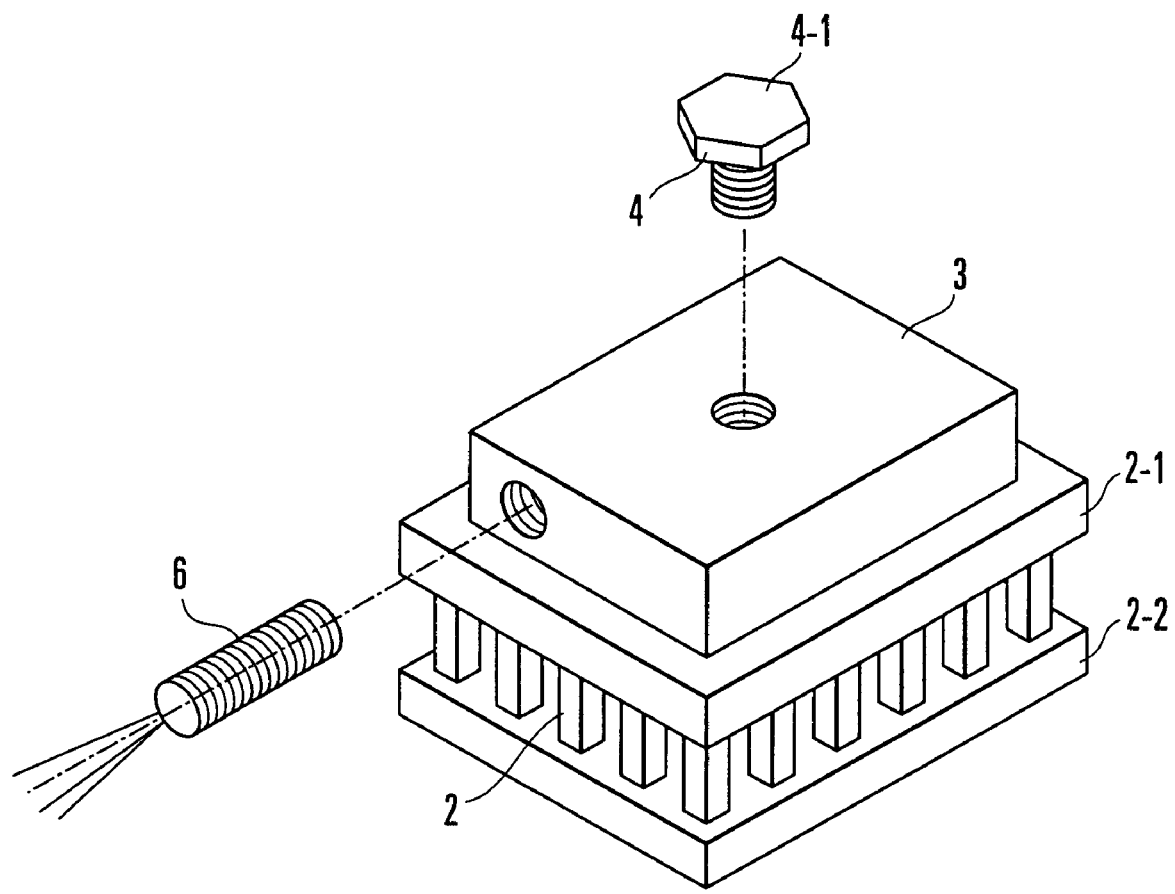
FIG. 12 is a perspective view showing a mounting structure for a mirror and temperature detection element in the conventional chilled mirror dew point hygrometer.

FIG. 9 is a schematic view showing the arrangement of a chilled mirror dew point hygrometer which shows another embodiment of the moisture detection device according to the present invention. In a chilled mirror dew point hygrometer 202, an optical fiber 17-1 on the light-emitting side and an optical fiber 17-2 on the light-receiving side are symmetrically arranged on the two sides of a mirror 10 instead of being coaxially arranged. The distal end portions of the optical fiber 17-1 on the light-emitting side and the optical fiber 17-2 on the light-receiving side, which are bent in the form of the letter "J", are directed to a mirror surface 10-1, and are symmetrically tilted at a predetermined tilt angle with respect to the mirror surface 10-1. Minute projections 10-2 are formed on the mirror surface 10-1 as in the first embodiment.

In the chilled mirror dew point hygrometer 202, a sensor unit 202A is placed in a gas to be measured. In addition, a dew condensation detecting unit 13 obliquely applies pulse light from the distal end portion of the optical fiber 17-1 to the mirror surface 10-1 of the mirror 10 at a predetermined period. The mirror surface 10-1 is exposed to the gas to be measured. If, therefore, no dew condensation has occurred on the mirror surface 10-1, almost the entire amount of pulse light applied from the distal end portion of the optical fiber 17-1 is specularly reflected, and is received through the optical fiber 17-2. Therefore, if no dew condensation has occurred on the mirror surface 10-1, the reflected pulse light received through the optical fiber 17-2 has a high intensity.

The dew condensation detecting unit 13 obtains the difference between the upper and lower limit values of reflected pulse light received through the optical fiber 17-2 as the intensity of the reflected pulse light, and sends a signal S1 corresponding to the intensity of the reflected pulse light to a Peltier output control unit 14. In this case, the intensity of the reflected pulse light is high and exceeds the threshold, and hence the Peltier output control unit 14 sends, to a signal conversion unit 15, a control signal S2 for increasing the current to the thermoelectric cooling element 2. With this operation, a current S3 from the signal conversion unit 15 to the thermoelectric cooling element 2 increases to lower the temperature of the cooling surface 2-1 of the thermoelectric cooling element 2.

As the temperature of the cooling surface 2-1 of the thermoelectric cooling element 2, i.e., the temperature of the mirror 10, lowers, water vapor contained in the gas to be measured condenses on the mirror surface 10-1 of the mirror 10. Part of light emerging from the distal end portion of the optical fiber 17-1 is absorbed and reflected diffusely by the molecules of the water. As a consequence, the intensity of the reflected light (specular reflection) from the mirror surface 10-1 which is received through the optical fiber 17-2 decreases.

If the intensity of the reflected pulse light received through the optical fiber 17-2 decreases below the threshold, the Peltier output control unit 14 sends, to the signal conversion unit 15, the control signal S2 for decreasing the current to the thermoelectric cooling element 2. This suppresses a drop in the temperature of a cooling surface 2-1 of the thermoelectric cooling element 2 and the occurrence of dew condensation. If the intensity of reflected pulse light received through the optical fiber 17-2 increases and exceeds the threshold with this suppression of dew condensation, the Peltier output control unit 14 sends, to the signal conversion unit 15, the control signal S2 for increasing the current to the thermoelectric cooling element 2. Repeating this operation adjusts the temperature of the cooling surface 2-1 of the thermoelectric cooling element 2 so as to make the intensity of the reflected pulse light received through the optical fiber 17-2 become almost equal to the threshold. This adjusted temperature, i.e., the temperature (dew-point temperature) at which dew condensation which has occurred on the mirror surface 10-1 has reached an equilibrium state is displayed as a dew-point temperature on a dew-point temperature display unit 12.

In the second embodiment as well, since the minute projections 10-2 are formed on the mirror surface 10-1 of the mirror 10, the projections 10-2 serve as nuclei to promote dew condensation, thereby improving responsiveness at a low dew point. In addition, this makes the sizes of condensed dew drops unlikely to change with a change in the flow rate of the gas to be measured, and makes the equilibrium state of dew condensation unlikely to break, thereby improving measurement accuracy.

Note that the first and second embodiments described above are configured to detect dew condensation (moisture) which occurs on the mirror surface 10-1. However, frost formation (moisture) which occurs on the mirror surface 10-1 can also be detected by the same arrangement as that described above.

In addition, the first and second embodiments described above use the thermoelectric cooling element (Peltier element) 2 as a cooling means for cooling the mirror 10. However, a helium refrigerator or the like may be used.

Furthermore, in the first and second embodiments, the projections 10-2 on the mirror surface 10-1 are formed by using, for example, a photoresist and etching. However, glass powder or diamond powder may be bonded to the mirror surface 10-1. Diamond is superior in heat conductivity and the like, and hence is promising.

INDUSTRIAL APPLICABILITY

The moisture detection device of the present invention can be used as a dew condensation meter which detects dew condensation which occurs on a mirror surface or a frosting meter which detects frost formation which occurs on a mirror surface.

The invention claimed is:

1. A moisture detection device comprising:
   a mirror whose mirror surface is exposed to a gas to be measured;
   a plurality of minute projections are formed at a predetermined interval on the mirror surface of said mirror;
   cooling means for cooling said mirror;
   light-emitting means for applying light to the mirror surface;
   light-receiving means for receiving reflected light of light applied from said light-emitting means to the mirror surface; and means for detecting moisture which is produced on the mirror surface of said mirror which is cooled by said cooling means on the basis of the reflected light received by said light-receiving means.

2. The moisture detection device according to claim 1, wherein the projection comprises a projection with a pointed tip.

3. The moisture detection device according to claim 1, wherein the projection comprises a columnar projection.

4. The moisture detection device according to claim 1, wherein the projection comprises a semispherical projection.

5. The moisture detection device according to claim 1, wherein said predetermined interval ranges from approximately 10 μm to approximately 50 μm.

6. The moisture detection device according to claim 5, wherein said plurality of minute projections are approximately 0.1 μm to approximately 1 μm in height and approximately 0.1 μm to approximately 1 μm across.

\* \* \* \* \*